US008933206B2

(12) United States Patent
Duffin et al.

(10) Patent No.: US 8,933,206 B2
(45) Date of Patent: Jan. 13, 2015

(54) BENZIMIDAZOLE COMPOUNDS AND THEIR USE AS CHROMATOGRAPHIC LIGANDS

(75) Inventors: Gordon R. Duffin, Felton (GB); Victoria Jane Dolan, Forest Hall (GB); Katherine Louise Angus, Washington (GB); Andrew Lyddiatt, Shotley Bridge (GB)

(73) Assignee: Millipore (U.K.) Limited, London (GB)

( * ) Notice: Subject to any disclaimer, the term of this patent is extended or adjusted under 35 U.S.C. 154(b) by 1210 days.

(21) Appl. No.: 12/008,117

(22) Filed: Jan. 8, 2008

(65) Prior Publication Data

US 2008/0262207 A1    Oct. 23, 2008

Related U.S. Application Data

(60) Provisional application No. 60/879,921, filed on Jan. 11, 2007.

(51) Int. Cl.
| | | |
|---|---|---|
| C07K 1/14 | (2006.01) | |
| G01N 33/537 | (2006.01) | |
| C07K 16/06 | (2006.01) | |
| C07D 235/06 | (2006.01) | |
| B01D 15/38 | (2006.01) | |
| B01J 20/289 | (2006.01) | |
| B01J 20/32 | (2006.01) | |
| C07D 403/04 | (2006.01) | |
| C07K 1/22 | (2006.01) | |

(52) U.S. Cl.
CPC .......... *C07K 16/065* (2013.01); *B01D 15/3804* (2013.01); *B01J 20/289* (2013.01); *B01J 20/3219* (2013.01); *B01J 20/3242* (2013.01); *B01J 20/3246* (2013.01); *B01J 20/3255* (2013.01); *C07D 235/06* (2013.01); *C07D 403/04* (2013.01); *C07K 1/22* (2013.01)
USPC ........ 530/413; 436/539; 436/541; 548/304.4; 548/310.7

(58) Field of Classification Search
CPC .............. B01D 15/3804; B01J 20/3219; B01J 20/3242; B01J 20/3255; B01J 20/3253; B01J 20/3246; C07K 1/22; C07K 16/065; C07D 235/06; C07D 403/04
See application file for complete search history.

(56) References Cited

U.S. PATENT DOCUMENTS

| | | | |
|---|---|---|---|
| 4,696,980 A | 9/1987 | Porath | |
| 4,701,500 A | 10/1987 | Porath | |
| 4,897,467 A | 1/1990 | Porath | |
| 5,141,966 A | 8/1992 | Porath | |
| 5,185,313 A | 2/1993 | Porath | |
| 5,502,022 A | 3/1996 | Schwartz et al. | |
| 5,652,348 A | 7/1997 | Burton et al. | |
| 5,719,269 A | 2/1998 | Schwarz et al. | |
| 5,942,463 A | 8/1999 | Oscarsson et al. | |
| 5,945,520 A | 8/1999 | Burton et al. | |
| 6,498,236 B1 | 12/2002 | Lihme et al. | |
| 6,610,630 B2 | 8/2003 | Schwarz et al. | |
| 6,919,436 B2 | 7/2005 | Lihme et al. | |
| 7,144,743 B2 | 12/2006 | Boschetti et al. | |
| 2004/0034037 A1 | 2/2004 | Harbeson et al. | |
| 2005/0187390 A1 | 8/2005 | Schmitz et al. | |

FOREIGN PATENT DOCUMENTS

| | | |
|---|---|---|
| DE | 26 38 551 A1 | 3/1977 |
| DE | 26 38 553 A1 | 5/1977 |
| EP | 0 764 048 B1 | 3/1997 |
| EP | 0 783 366 B1 | 7/1997 |
| EP | 0 764 049 B1 | 9/2001 |
| EP | 0 921 855 B1 | 11/2003 |
| GB | 1562812 | 3/1980 |
| GB | 1562823 | 3/1980 |
| WO | WO 95/31279 A1 | 11/1995 |
| WO | WO 95/33557 A1 | 12/1995 |
| WO | WO 96/00735 A1 | 1/1996 |
| WO | WO 96/09116 A1 | 3/1996 |
| WO | WO 98/08603 A1 | 3/1998 |
| WO | WO 2004/039765 A1 | 5/2004 |
| WO | WO 2005/073711 A2 | 8/2005 |

OTHER PUBLICATIONS

Carredano, E., et al., "A Novel and Conserved Pocket of Human κ-Fab Fragments: Design, Synthesis, and Verification of Directed Affinity Ligands," *Protein Science*, 13:1476-1488 (2004).
Product Notice, "MBI HyperCel™ Mixed-mode sorbent for direct capture of antibodies," Ciphergen Biosystems, Inc.: 1-8 (2004).
Brenac, V., et al., "Capture of a monoclonal antibody and prediction of separation conditions using a synthetic multimodal ligand attached on chips and beads," *Journal of Chromatography B.*, 818(1): 61-66 (2005).
Girot, P., et al., "2-Mercapto-5-benzimidazolesulfonic acid: an effective multimodal ligand for the separation of antibodies," *Journal of Chromatography B.*, 808(1): 25-33 (2004).
European Search Report for European Patent Application No. 08250127.1, filed Jan. 10, 2008.
Written Opinion from Hungarian Patent Office for Singapore Patent Application No. SG 200800028-3, mailed May 13, 2010.
Communication with Extended European Search Report from European Patent Office, dated Jun. 6, 2011, from Application No. 11159874.4-1222, consisting of 10 pages.
Communication from EPO of Office Action for EP Application No. 08250127.1-1222/1944311, dated Mar. 25, 2009.

*Primary Examiner* — Shafiqul Haq
(74) *Attorney, Agent, or Firm* — Hamilton, Brook, Smith & Reynolds, P.C.

(57) ABSTRACT

The present invention provides a new method for isolation and/or purification of immunoglobulins from a solution containing one or more immunoglobulins using a solid phase matrix represented by the formula: M-SP-L, wherein M is designates a matrix backbone, SP designates a spacer and L designates a substituted benzimidazole ligand.

31 Claims, No Drawings

BENZIMIDAZOLE COMPOUNDS AND THEIR USE AS CHROMATOGRAPHIC LIGANDS

RELATED APPLICATION

This application claims the benefit of U.S. Provisional Application No. 60/879,921, filed on Jan. 11, 2007. The entire teachings of the above application is incorporated herein by reference.

BACKGROUND OF THE INVENTION

Immunoglobulins or antibodies constitute a very important class of proteins which are present in various body fluids of mammals, birds and fish functioning as protective agents of the animal against substances, bacteria and virus challenging the animal. Immunoglobulins are typically present in animal blood, milk, and saliva as well as other body fluids and secretions.

The biological activity, which the immunoglobulins possess, is today exploited in a range of different applications in the human and veterinary diagnostic, health care and therapeutic sectors.

All the above mentioned applications of immunoglobulins require some sort of isolation of the antibody from the crude raw material, but each kind of application has its own varying demands with respect to the final purity and allowable cost of the antibody product.

Generally, there exists a very broad range of different methods available for isolation of immunoglobulins giving a very broad range of final purities, yields and cost of the product.

Traditional methods for isolation of immunoglobulins are based on selective reversible precipitation of the protein fraction comprising the immunoglobulins while leaving other groups of proteins in solution. Typical precipitation agents being ethanol, polyethylene glycol, lyotropic (anti-chaotropic) salts such as ammonium sulfate and potassium phosphate, and caprylic acid.

Typically, these precipitation methods are giving very impure products while at the same time being time consuming and laborious. Furthermore, the addition of the precipitating agent to the raw material makes it difficult to use the supernatant for other purposes and creates a disposal problem. This is particularly relevant when speaking of large scale purification of immunoglobulins from, e.g., whey and plasma.

Ion exchange chromatography is another well known method of protein fractionation frequently used for isolation of immunoglobulins. However, this method is not generally applicable because of the restraints in ionic strength and pH necessary to ensure efficient binding of the antibody together with the varying isoelectric points of different immunoglobulins.

Protein A and Protein G affinity chromatography are very popular and widespread methods for isolation and purification of immunoglobulins, particularly for isolation of monoclonal antibodies, mainly due to the ease of use and the high purity obtained. Although being popular, it is however recognized that Protein A and Protein G pose several problems to the user, among which are: very high cost, variable binding efficiency of different monoclonal antibodies (particularly mouse $IgG_1$), leakage of Protein A/Protein G into the product, and low stability of the matrix in typical cleaning solutions, e.g., 1 M sodium hydroxide. Each of these drawbacks have its specific consequence in the individual application, ranging from insignificant to very serious and prohibitive consequences.

Therefore, there is a need for new methods for isolation and purification of immunoglobulins.

SUMMARY OF THE INVENTION

The invention is based upon the discovery that solid phase matrix, formed by linking certain substituted benzimidazole ligand to a solid phase material, can be utilized in a method for the isolation and/or purification of immunoglobulins of different kinds from widely different raw materials with high efficiency and with special advantages with respect to the use of little or no salts, especially lyotropic salts, in the binding process and with respect to the ability to bind a wide range of immunoglobulins. Furthermore, these matrices have special advantages with respect to stability in NaOH, which is especially relevant when the solid phase matrices are to be regenerated after use.

One embodiment of the present invention is directed to a method for the isolation of immunoglobulins from a solution containing one or more immunoglobulins, comprising: a) contacting the solution containing one or more immunoglobulins with a solid phase matrix of the general formula: M-SP-L; b) separating the solid phase matrix having immunoglobulins bound thereto from the solution; c) optionally washing the solid phase matrix; and d) contacting the solid phase matrix with an eluent in order to liberate the one or more immunoglobulins from the solid phase matrix.

M designates the matrix backbone, SP designates a spacer, and L designates a ligand represented by structural formula (I):

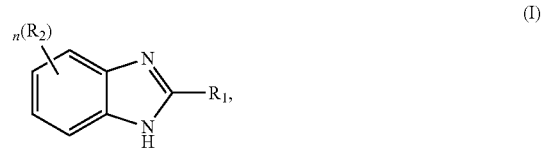

or a tautomer thereof, wherein:
 $R_1$ is —Z—N($R_3$)$_2$, —Z—S$R_3$, or —Z—O$R_3$;
 $R_2$ is —H, -halogen (e.g., —F, —Cl, —Br, or —I), —O$R_4$, —NH$_2$, -alkyl, —NO$_2$, —SO$_3$H, —N($R_3$)C(O)N($R_3$)$_2$

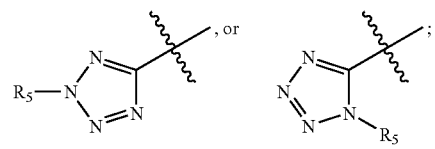

$R_3$, for each occurrence, is independently —H or a substituted or unsubstituted alkyl;
 $R_4$, for each occurrence, is independently —H or a substituted or unsubstituted alkyl;
 $R_5$, for each occurrence, is independently —H or a substituted or unsubstituted alkyl;
 Z is a single bond, a substituted or unsubstituted alkylene, a substituted or unsubstituted alkenylene or a substituted or unsubstituted alkynylene;
 n is an integer from 0 to 4, provided L is not 2-mercapto-5-nitro-benzimidazole, 2-amino-benzimidazole, 2-mercaptobenzimidazole, and 2-aminomethyl-benzimidazole.

The present invention further provides a solid phase matrix, comprising a functionalized matrix backbone carrying a plurality of functional groups represented by the following formula: M-SP-L.

The present invention is also directed to a compound represented by the following structural formulas:

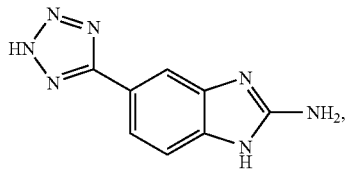

1

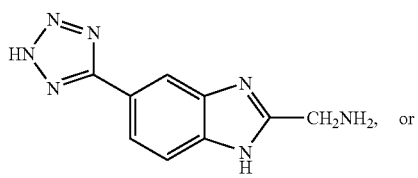

2

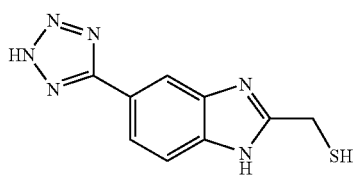

3

The solid phase matrix and the method of the present invention can be used to isolate and/or purify immunoglobulins with high efficiency and high purity.

DETAILED DESCRIPTION OF THE INVENTION

The present invention is directed to a method of isolating and/or purifying immunoglobulin comprising contacting a solution containing one or more immunoglobulins with solid phase matrices described herein. The present invention is also directed to the solid phase matrices described herein. Thus, the definitions below relate to the method according to the invention as well as to the solid phase matrices according to the invention. The present invention is also directed to certain ligands for making the solid phase matrices described herein.

Solid Phase Matrices

As described above, the method according to the invention includes the use of a solid phase matrix, where the solid phase matrix comprises a functionalized matrix backbone carrying a plurality of functional groups represented by the following formula:

M-SP-L, wherein M designates the matrix backbone, SP designates a spacer, and L designates a ligand represented by the structural formula (I):

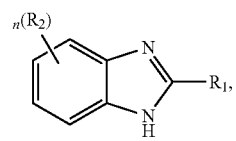

or a tautomer thereof, wherein
$R_1$ is —Z—N($R_3$)$_2$, —Z—SR$_3$, or —Z—OR$_3$;
$R_2$ is —H, -halogen, —OR$_4$, —NH$_2$, -alkyl, —NO$_2$, —SO$_3$H, —N($R_3$)C(O)N($R_3$)$_2$ or

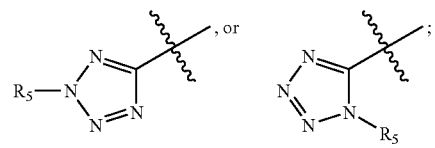

$R_3$, for each occurrence, is independently —H or an optionally substituted alkyl;
$R_4$, for each occurrence, is independently —H or an optionally substituted alkyl;
$R_5$, for each occurrence, is independently —H or an optionally substituted alkyl;
Z is a single bond, an optionally substituted alkylene, an optionally substituted alkenylene or an optionally substituted alkynylene;
n is an integer from 0 to 4;
provided L is not 2-mercapto-5-nitro-benzimidazole, 2-amino-benzimidazole, 2-mercaptobenzimidazole, and 2-aminomethyl-benzimidazole.

In one embodiments, $R_1$ is —Z—N($R_3$)$_2$, —Z—SR$_3$, or —Z—OR$_3$. In another embodiment, $R_1$ is —NH$_2$, —SH, —CH$_2$SH or —CH$_2$—NH$_2$.

In one embodiment, Z is a single bond, an optionally substituted alkylene, an optionally substituted alkenylene, or an optionally substituted alkynylene. In another embodiment, Z is a C1-C10 alkylene. In another embodiment, Z is a C1-C5 alkylene. In another embodiment, Z is a single bond.

In one embodiment, $R_2$, for each occurrence, is independently —H, -halogen, —OR$_4$, —NH$_2$, -alkyl, —NO$_2$, —SO$_3$H, —N($R_3$)C(O)N($R_3$)$_2$,

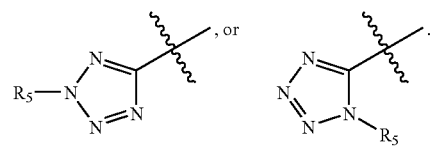

In one embodiment, $R_2$ is

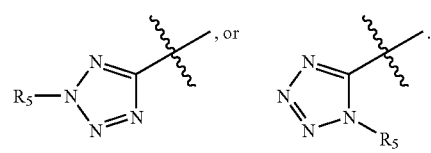

Preferably, $R_5$ is H. In another embodiment, $R_2$ is —H. In another embodiment, $R_2$ is a C1-C10 alkyl. In another embodiment, $R_2$ is a C1-C5 alkyl.

In one embodiment, $R_3$, for each occurrence, is independently —H or an optionally substituted alkyl. In one embodiment, $R_3$ is —H. In another embodiment, $R_3$ is a C1-C10 alkyl. In another embodiment, $R_3$ is a C1-C5 alkyl.

In one embodiment, $R_4$, for each occurrence, is independently —H or an optionally substituted alkyl. In one embodiment, $R_4$ is —H. In another embodiment, $R_4$ is a C1-C10 alkyl. In another embodiment, $R_4$ is a C1-C5 alkyl.

In one embodiment, $R_5$, for each occurrence, is independently —H or an optionally substituted alkyl. In one embodiment, $R_5$ is —H. In another embodiment, $R_5$ is a C1-C10 alkyl. In another embodiment, $R_5$ is a C1-C5 alkyl.

In one embodiment, n is an integer from 0 to 4. In another embodiment, n is 1. In another embodiment, n is 0.

In a specific embodiment, Z is a C1-C10 alkyl; $R_3$, for each occurrence, is independently —H or a C1-C10 alkyl; $R_4$, for each occurrence, is independently —H or a C1-C10 alkyl; $R_5$, for each occurrence, is independently —H or a C1-C10 alkyl.

In another specific embodiment, Z is a C1-C5 alkyl; $R_3$, for each occurrence, is independently —H or a C1-C5 alkyl; $R_4$, for each occurrence, is independently —H or a C1-C5 alkyl; $R_5$, for each occurrence, is independently —H or a C1-C5 alkyl.

In another specific embodiment, ligand L is represented by structural formula (I), wherein Z is a single bond; n is 1 and other variables are as described above for structural formula (I). In a more specific embodiment, Z is a single bond; n is 1; $R_3$, for each occurrence, is independently —H or a C1-C10 alkyl; $R_4$, for each occurrence, is independently —H or a C1-C10 alkyl; and $R_5$, for each occurrence, is independently —H or a C1-C10 alkyl. In another more specific embodiment, Z is a single bond; n is 1; $R_3$, for each occurrence, is independently —H or a C1-C5 alkyl; $R_4$, for each occurrence, is independently-H or a C1-C5 alkyl; and $R_5$, for each occurrence, is independently —H or a C1-C5 alkyl.

In another specific embodiment, ligand L is represented by the structural formula (II):

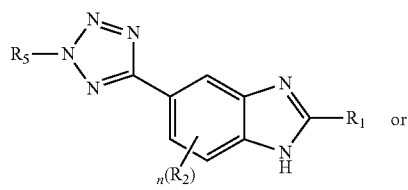

(II)

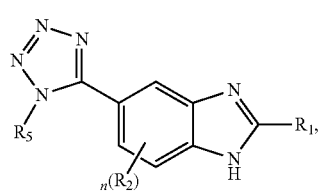

or a tautomer thereof, wherein variables are as described above for structural formula (I). In a more specific embodiment, $R_5$ is —H. In another more specific embodiment, Z is a single bond or a C1-C5 allyl; and $R_5$ is —H.

In another specific embodiment, the ligand L is represented by structural formula (III):

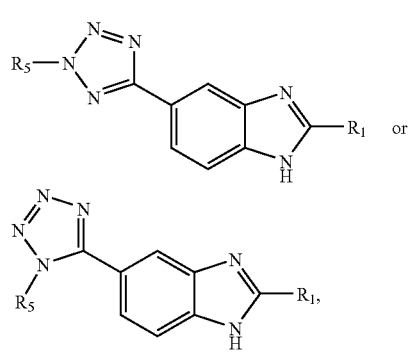

(III)

or a tautomer thereof, wherein variables are as described above for structural formula (I). In a more specific embodiment, $R_5$ is —H. In another more specific embodiment, Z is a single bond or a C1-C5 alkyl; and $R_5$ is —H.

In certain embodiments, L is represented by the following structural formulas:

1

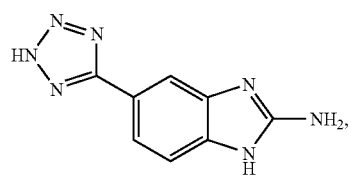

2

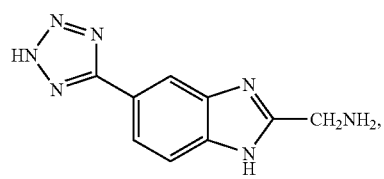

3

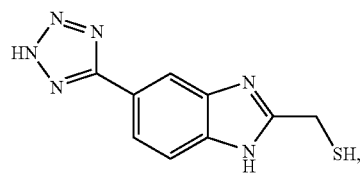

4

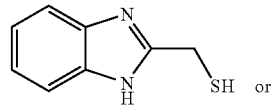

5

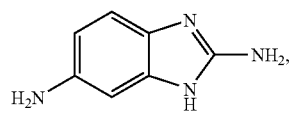

or a tautomer thereof.

Even though the ligands are named or depicted by structural formula herein and in the following using the nomenclature corresponding to the individual and discrete chemical compound, from which they are derived, it should be understood that the actual ligand L is a radical of such a compound. Ligand can be linked to the matrix backbone at different connecting position of the ligand. The connecting position varies depending on the identity of the ligand. The connecting position of the ligand is the most reactive position of the ligand under the reaction condition for linking the ligand to the matrix backbone. For example, ligand can be linked at the benzimidazole nitrogen, represented by the following structural formula with the connecting position denoted with "⌇":

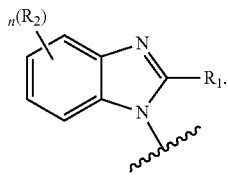

In certain embodiments, when $R_1$ is represented by —Z—$NHR_3$, —Z—SH, or —Z—OH, wherein Z is not a single bond, -L can be represented by the following structural formula:

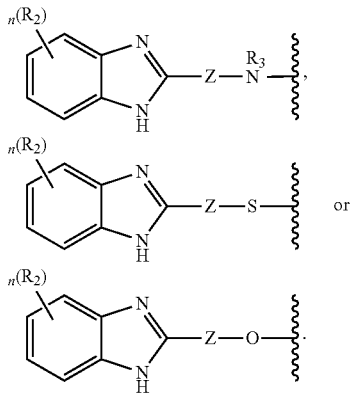

In certain instances, tautomeric forms of the disclosed ligand exist, such as the tautomeric structures shown below:

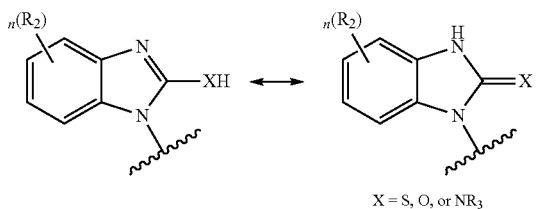

X = S, O, or $NR_3$

It is to be understood that when a ligand is named or represented by a structural formula herein, all other tautomeric forms which may exist for the compound are encompassed by the structural formula.

The solid phase matrix may comprise, as the matrix backbone, any natural or synthetic and organic or inorganic material known per se to be applicable in solid phase separation of proteins and other biomolecules, e.g., natural or synthetic polysaccharides such as agar-agar and agaroses; celluloses, cellulose ethers such as hydroxypropyl cellulose, carboxymethyl celluose; starches; gums such as guar gum, and gum arabic, gum ghatti, gum tragacanth, locust bean gum, xanthan gum; pectins; mucins; dextrans; chitins; chitosans; alginates; carrageenans; heparins; gelatins; synthetic polymers such as polyamides such as polyacrylamides and polymethacrylamides; polyimides; polyesters; polyethers; polymeric vinyl compounds such as polyvinylalcohols and polystyrenes; polyalkenes; inorganic materials such as silicious materials such as silicon dioxide including amorphous silica and quartz; silicas; metal silicates, controlled pore glasses and ceramics; metal oxides and sulfides, or combinations of these natural or synthetic and organic or inorganic materials.

The matrix backbone is preferably selected from agar-agar, agaroses, celluloses, cellulose ethers such as hydroxypropyl cellulose, carboxymethyl cellulose, polyamides such as poly (meth)acrylamides, polyvinylalcohols, silicas, and controlled pore glasses.

Especially interesting solid phase materials as matrix backbones are, e.g., agar or agarose beads such as Sepharose and Superose beads from Pharmacia Biotech, Sweden and Biogel A from Biorad, USA; dextran based beads such as Sephadex, Pharmacia Biotech; cellulose based beads and membranes such as Perloza cellulose from Secheza, Czechoslovakia; composite beads such as Sephacryl and Superdex, Pharmacia Biotech; beads of synthetic organic polymers such as Fractogel from Toso-Haas, USA; POROS media from Perceptive Biosystems, USA, Bio-Rex, Bio-Gel P and Macro Prep from Biorad, HEMA and Separon from TESSEK and Hyper D and Trisacryl media from BioSepra, USA, Enzacryl and Azlactone, 3M, USA; beads of siliceous materials such as controlled pore glass, PROSEP, from Bioprocesing, England and Spherocil, BioSepra; and coated silica composites in the form of beads or membranes such as ACTI-DISK, ACTI-MOD and CycloSep from Arbor Technologies, USA.

Typically, the matrix backbone, as well as the resulting functionalized solid phase matrix, may, for example, be in the form of irregular particles or spherical beads, membranes or sheets, molded surfaces, or stick. The solid phase material may further be fully or partly permeable or completely impermeable to proteins. In a particularly interesting embodiment of the present invention, the matrix is in the form of irregular spherical beads with sizes in the range of 1-10000 µm, preferably 10-1000 µm; such as 10-60 µm for high performance applications and such as 50-500 µm, preferably 50-300 µm, for preparative purposes.

A particular interesting form of matrix is a density controlled matrix in the form of a conglomerate comprising density controlling particles. These conglomerates, which are especially applicable in large scale operations for fluidized or expanded bed chromatography as well as different batch-wise chromatography techniques in non-packed columns, e.g., simple batch adsorption in stirred tanks, are described in the WO 92/00799, which is hereby incorporated by reference in its entirety.

The ligands L may be attached to the solid phase material by any type of covalent bond known per se to be applicable for this purpose, either by a direct chemical reaction between the ligand and the solid phase material or by a preceding activation of the solid phase material or of the ligand with a suitable reagent known per se making it possible to link the matrix backbone and the ligand. Examples of such suitable activating reagents are epichlorohydrin, epibromohydrin, allyl glycidylether; bis-epoxides such as butanedioldiglycidylether; halogen-substituted aliphatic compounds such as di-chloropropanol, divinyl sulfone; carbonyldiimidazole; aldehydes such as glutaric dialdehyde; quinones; cyanogen bromide; periodates such as sodium-meta-periodate; carbodiimides; chloro-triazines such as cyanuric chloride; sulfonyl chlorides such as tosyl chlorides and tresyl chlorides; N-hydroxy succinimides; 2-fluoro-1-methylpyridinium toluene-4-sulfonates; oxazolones; maleimides; pyridyl disulfides;

hydrazides; and allyl bromide/bromine. Among these, the activating reagents leave a spacer group SP different from a single bond, e.g., epichlorohydrin, epibromohydrin, allyl-glycidylether; bis-epoxides; halogen-substituted aliphatic compounds; divinyl sulfone; aldehydes; quinones; cyanogen bromide; chloro-triazines; oxazolones; maleimides; pyridyl disulfides; and hydrazides. In a specific embodiment, the spacer SP is represented by the formula: (O—$CH_2$CH(OH)—$CH_2)_m$—, wherein m is an integer from 1 to 10. More specifically, m is an integer from 1 to 5. Even more specifically, m is an integer from 1 to 3.

In certain instances, the activating reagent may even constitute a part of the functionality contributing to the binding of immunoglobulins to the solid phase matrix, e.g., in cases where divinyl sulfone is used as the activating reagent. In other cases the activating reagent is released from the matrix during reaction of the functional group with the matrix. This is the case when carbodiimidazoles and carbodiimides are used.

In a specific embodiment, the activating agent is allyl bromide/bromine.

The above mentioned possibilities makes it relevant to define the presence of an optional spacer SP linking the matrix M and the ligand L. In the present context, the spacer SP is to be considered as the part of the activating reagent which forms the link between the matrix and the ligand. Thus, the spacer SP corresponds to the activating reagents and the coupling reactions involved. In some cases, e.g., when using carbodiimides, the activating reagent forms an activated form of the matrix or of the ligand reagent. After coupling, no parts of the activating reagent is left between the ligand and the matrix, and, thus, SP is simply a single bond.

In other cases, the spacer SP is an integral part of the functional group effecting the binding characteristics, i.e., the ligand, and this will be especially significant if the spacer SP comprises functionally active sites or substituents such as thiols, amines, acidic groups, sulfone groups, nitro groups, hydroxy groups, nitrile groups or other groups able to interact through hydrogen bonding, electrostatic bonding or repulsion, charge transfer or the like.

In still other cases, the spacer SP may comprise an aromatic or heteroaromatic ring which plays a significant role for the binding characteristics of the solid phase matrix. This would for example be the case if quinones or chlorotriazines where used as activation agents for the solid phase matrix or the ligand.

In certain embodiments, the spacer SP is a single bond or a biradical derived from an activating reagent selected from epichlorohydrin, allyl-glycidylether, bis-epoxides such as butanedioldiglycidylether, halogen-substituted aliphatic compounds such as 1,3-dichloropropan-2-ol, aldehydes such as glutaric dialdehyde, divinyl sulfone, quinones, cyanogen bromide, chloro-triazines such as cyanuric chloride, 2-fluoro-1-methylpyridinium toluene-4-sulfonates, maleimides, oxazolones, and hydrazides.

In certain embodiments, the spacer SP is selected from short chain aliphatic biradicals, e.g., of the formula —$CH_2$—CH(OH)—$CH_2$— (derived from epichlorohydrin), —$(CH_2)_3$ O—$CH_2$—CH(OH)—$CH_2$— (derived from allyl-glycidylether) or —$CH_2$—CH(OH)—$CH_2$—O—$(CH_2)_4$—O—$CH_2$—CH(OH)—$CH_2$— (derived from butane-dioldig-lycidylether); or a single bond.

Due to the risk of leakage of material (e.g., the ligand and/or the spacer) from a solid phase matrix into the eluted product (e.g., the immunoglobulin) the molecular weight of the ligand (or the ligand+the optional spacer) is advantageously chosen as low as possible. A major drawback of using protein A, protein G, synthetic peptides and other relatively high molecular weight ligands (e.g., dyes) is that it may be difficult or even impossible to separate any released ligand (optionally including the spacer) from the eluted immunoglobulin due to the small difference between the respective molecular weights and the natural tendency of the components to bind to, each other. This may have a detrimental effect in those cases where the immunoglobulin is to be used as a therapeutic agent causing allergic shock or other serious symptoms in the patient. The smaller the molecular weight of the ligand (including its spacer) the more efficient can any leaked ligand be separated from the immunoglobulin product. Another significant advantage of having the smallest possible molecular weight of the ligand (or the ligand-spacer arm conjugate) is that any leaked material which may not have been separated from the immunoglobulin prior to injection/ingestion in the patient will elucidate a minimum of antigenicity the lower the molecular weight and therefore in general be relatively more acceptable to the organism than higher molecular weight ligands.

It is therefore preferred that the ligand L has a molecular weight below 500 Dalton, preferably below 400 Dalton, more preferably below 300 Dalton, such as below 250 Dalton, or even below 200 Dalton.

With respect to the ligand-spacer arm conjugate (-SP-L), it is preferred that the molecular weight is below 500 Dalton, more preferably below 400 Dalton, such as below 300 Dalton, or even below 260 Dalton.

According to the invention, the matrix comprises ligands which either alone or in combination with a spacer SP (and even the matrix backbone) make it possible to bind immunoglobulins thereto. It is found that a crucial part of the ligand is a substituted benzimidazole.

It is envisaged that a combination of two or more of the different ligands defined herein on the same matrix backbone may lead to certain advantages with respect to high binding efficiency and/or high purity of the immunoglobulin. However, in an important embodiment of the present invention, all of the functional groups on the solid phase matrix are substantially identical.

It may also be found to enhance binding efficiency and purity of the product by coupling the ligand to a matrix already comprising negatively or positively charged moieties such as positively charged amino-groups or negatively charged carboxylic acid, sulfonic acid or phosphonic acid groups.

The ligand concentration may also be of major significance for the functional characteristics of a matrix according to the invention, e.g., a ligand may show a high degree of selective binding of immunoglobulins at one ligand concentration, while an increase in the ligand concentration results in a decrease in the binding selectivity. As is well-known to a person skilled in the art too high ligand concentrations may lead to strong binding of unwanted impurities by mechanism of multiple binding points, because the ligands are too closely spaced on the solid phase backbone. If the ligand concentration is kept low, the ligands will be spaced with larger distances and therefore not cause the binding of impurities by binding at multiple sites. Another negative effect of too high ligand concentration is the risk of binding the wanted protein, e.g., the immunoglobulin by multiple binding sites. Such a multiple binding may lead to difficulties in releasing the protein, e.g., the immunoglobulin with an appropriate elution buffer. In some instances, it may even be necessary to utilize strongly denaturing conditions and/or organic solvents for release of the product from such to highly substituted solid phase matrices—with loss of biological activity as a consequence.

Ligand concentration of solid phase matrices may be disclosed in several different ways. One way of describing the ligand concentration is to disclose the amount of ligand present per gram of dry matter (e.g., in µmol/g dry matter). This is the result obtained directly if for example the ligand concentration is measured by elemental analysis of dried (e.g., freeze-dried) samples of the solid phase matrix. The ligand concentration may, however, also be disclosed as the amount of ligand present on one ml wet and sedimented solid phase matrix (also often referred to as one ml packed bed matrix). This is a figure which is easily calculated from a determination based on dried solid phase matrix (e.g., µmol/g dry matter), if the dry matter content of the hydrated solid phase matrix has been determined at the same time (i.e., gram of dry matter/ml wet sedimented solid phase matrix). Still another way of disclosing the ligand concentration is as the amount of ligand present in one gram of wet, but suction drained matrix. This figure is again easily calculated from a determination based on dry matter, if the solid phase dry matter content per gram of wet, but suction drained matrix has been determined at the same time.

Thus, the ligand concentration of the solid phase matrices of the invention is preferably in the range of 10-990 µmol/g dry matter of solid phase matrix, such as 100-990 µmol/g, more preferably 200-980 µmol/g, in particular 250-975 µmol/g; or the ligand concentration the solid phase matrices of the invention is preferably in the range of 1-145 µmol/ml of hydrated, sedimented solid phase matrix, such as 10-120 µmol/ml, more preferably 15-100 µmol/ml, in particular 20-80 µmol/ml; or the ligand concentration the solid phase matrices of the invention is preferably in the range of 1-130 µmol/g wet, but suction drained solid phase matrix, such as 10-110 µmol/g, more preferably 20-100 µmol/g, in particular 20-90 µmol/g.

Synthesis of Solid Phase Matrices

Generally a solid phase matrix may be derivatized so as to comprise covalently linked ligands of the present invention according to methods know per se, e.g., activation of the matrix backbone with a suitable reagent known per se followed by coupling of the ligand to the activated matrix backbone, optionally incorporating a spacer SP between the ligand and the matrix backbone by coupling the spacer to the activated matrix backbone first followed by coupling the ligand to the spacer via a suitable condensation reagent or even a second activation of the spacer followed by coupling of the ligand.

The sequence and choice of reagents may depend on the actual ligand to be coupled and the matrix backbone to be derivatized with consideration to, e.g., the content of reactive groups such as hydroxyl, amino, mercapto, and silanols etc. In some cases, it may be preferable to activate or derivatize the ligand instead of the matrix backbone followed by a reaction of the derivatized ligand with the solid phase matrix backbone.

Thus, in a preferred method for synthesizing a solid phase matrix according to the invention, the matrix backbone is first reacted with a reagent able to react with the matrix backbone and thereby activate it for further reaction with the ligand, optionally washing away the activation reagent followed by a reaction of the activated matrix backbone with a solution comprising the ligand and optionally followed by washing the solid phase matrix comprising the covalently immobilized ligand with one or more suitable solutions cleaning the matrix for surplus reactants.

In some cases, in may be possible to combine the activation and the coupling of the ligand by mixing the two reagents and let the reactions take place in parallel. This is a great advantage as it saves costs and time as well as minimizing the volume of waste water. Thus, the activation and the coupling step is preferably performed in one combined step.

Furthermore, it is a significant advantage if the activation and/or the coupling reaction can be performed without the need to add organic solvents to the reaction medium. These organic solvents are often used to solubilize the reactive reagents or to ensure that hydrolysis of reactive species are kept at a minimum. However, the use of organic solvents adds to the cost and risk of the process because of the risk of explosions, the risk of health damage, the waste problems and the relatively high cost of the solvents themselves. Thus, the activation and/or the coupling procedure is preferably performed without the addition of any organic solvent to the reaction medium.

In certain embodiments, the present invention is directed to a compound represented by structural formulas (I), (II) and (III) described above. In a specific embodiment, the compound of the present invention is selected from the following structural formulas:

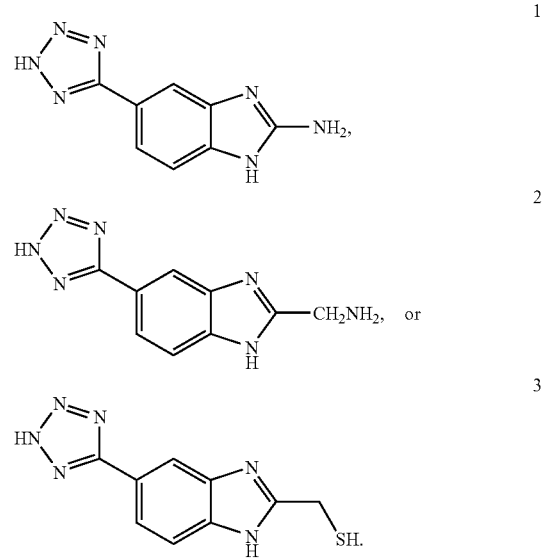

The compounds described above serve as ligands for preparing solid phase matrices of the present invention described herein.

Isolation of Immunoglobulins

In general, the method of the present invention for isolation of immunoglobulins may be divided into several steps: (a) equilibration of the solid phase matrix; (b) contacting the solid phase matrix with immunoglobulin solution; (c) washing the solid phase; (d) separation of the solid phase from the solution; (d) elution of the bound immunoglobulin; (e) regeneration of the solid phase matrix.

It may, however, depend on the specific application whether all steps are performed each time or at all. Thus, the only mandatory steps are the contacting, separation, and the elution steps, while the equilibration, washing, and regeneration steps may or may not be performed according to the specific requirements relevant to the actual application. The type of the separation step depends on the actual set-up (see below).

Equilibration

Before contacting the solid phase matrix with the immunoglobulin containing solution, it is preferred to ensure that both the matrix and the solution are in a condition resulting in the wanted binding of immunoglobulin. In this respect, it may therefore be necessary to adjust parameters such as pH, ionic strength, and temperature and in some instances, the addition of substances of different kind to promote binding of immunoglobulins and/or to prevent binding of impurities.

Thus, it is an optional step to perform an equilibration of the solid phase matrix by washing it with a solution (e.g., a buffer for adjusting pH, ionic strength, etc., or for the introduction of a detergent) bringing the necessary characteristics to the solid phase.

Contacting

When the solid phase matrix is in the form of particles of either spherical or irregular form, the contacting of a solution containing one or more immunoglobulins may be performed either in a packed bed column or in a fluidized/expanded bed column containing the solid phase matrix. It may also be performed in a simple batch operation where the solid phase matrix is mixed with the solution for a certain time to allow binding of the immunoglobulin(s).

Whenever the solid phase matrix is in the form of permeable or semi-permeable membranes or sheets, the contacting is generally performed by pumping/forcing the immunoglobulin containing solution across the surface and/or through a porous structure of the membrane or sheet to ensure that the immunoglobulins are coming in close contact with the ligands immobilized on the surface and/or in the porous structures.

Further guidelines for this process are given in "Purification Tools for Monoclonal Antibodies", Gagnon, P., Validated Biosystems, 1996.

Washing

After contacting the solid phase matrix with the immunoglobulin containing solution, there is an optionally performed washing procedure to remove unbound or loosely bound substances such as other proteins, lipids, nucleic acids or other impurities from the matrix. However, in some cases where very high purity of the immunoglobulin is not critical, the washing procedure may be omitted saving a process-step as well as washing solution.

In other cases where very high purity of the immunoglobulin is needed, there may be employed several different washing procedures with different washing buffers before elution is commenced.

The washing buffers employed will depend on the nature of the chromatographic adsorbent and the ligand binding the immunoglobulins. The washing buffer should not disturb the binding of the immunoglobulin to the adsorbent, i.e., pH, salt concentration and other additives should be adjusted so that only the unwanted impurities are removed either by simple substitution of the solution containing impurities and present in and around the adsorbent with the washing buffer—or in combination herewith also releasing impurities bound to the adsorbent. The releasing of impurities bound to the matrix may be accomplished either by changing pH and/or ionic strength or by adding a substance to the washing buffer which interacts competitively with either the adsorbent or the impurity, and thereby displacing the impurity from the adsorbent.

The washing (operation (c) in the method according to the invention) is preferably performed in order to remove remainders from the solution containing the immunoglobulins, and in order to remove other type of biomolecules.

Elution

Elution of the bound immunoglobulin is generally performed by contacting the solid phase matrix comprising the bound immunoglobulins with a solution that releases the immunoglobulin from the ligand on the matrix. The immunoglobulin is hereby released into the solution and can be washed out of the matrix. The solution employed to release the immunoglobulin should generally have different characteristics than what was used for binding of the immunoglobulin, e.g., the solution may have a different pH, a different ionic strength, a different temperature and/or it may comprise organic solvents (preferably only small amounts), detergents, chaotropes or other denaturing reagents. Combinations of changes in these different parameters are also generally employed.

Elution may also be performed by applying a solution gradually changing the conditions from binding to non-binding conditions, a procedure which typically is phrased gradient elution.

Once the immunoglobulin have been released from the solid phase matrix into the eluting solution, it may be recovered from this by different optional means known per se. In the most simple case, the immunoglobulin may be used directly without any changes but in many instances some sort of concentrating procedure would be preferred e.g., ultrafiltration, freeze-drying or precipitation (e.g., salting out). The immunoglobulin solution may also very well be purified further in a further processing step of optional character.

Regeneration

The solid phase matrix may optionally be cleaned, i.e., regenerated after elution of the immunoglobulin. This procedure is typically performed regularly to minimize the building up of impurities fouling up the surface of the solid phase and/or to sterilize the matrix to avoid contamination of the product with microorganisms proliferating and escaping from the solid phase and the equipment used during the process. A standard method of performing such a regeneration step is to wash the solid phase matrix with solutions able to clean the matrix and/or kill microorganisms. Typical solutions for these purposes would be, e.g., 0.1-1.0 M sodium hydroxide; solutions of peracids or hydrogen peroxide; denaturants such as guanidinium hydrochloride; solutions comprising active chlorine such as hypochlorite solutions, organic solvents such as ethanol; detergents etc. An especially preferred method for this purpose is to use 0.1-1.0 M sodium hydroxide due to the very high efficiency, low cost, ease of neutralization with hydrochloric acid and lack of waste problems.

In a specific embodiment of the present invention, the method includes: (i) equilibration (optional step), (ii) contacting, (iii) washing (optional step), (iv) separation, (v) elution, and (vi) regeneration, where cycle of steps (i)-(v) are repeated one or several times before regeneration, and the solid phase matrix is reused after regeneration.

The conditions employed in both the binding, washing and elution step(s) may be very decisive for the resulting binding efficiency, yield and purity of the immunoglobulin. Different solid phase matrices according to the invention may need different binding, washing and elution conditions to ensure an optimal result. Likewise, the nature of the raw material will have a very significant impact on the conditions chosen for that particular isolation procedure, e.g., very dilute solutions of monoclonal antibodies in hybridoma cell culture supernatants (typically 10-100 µg/ml) behave differently than the same type of antibodies present in more concentrated solutions such as ascites fluids (1-5 mg/ml) and immunoglobulins present in, e.g., whey (1-2 mg/ml) need other conditions than immunoglobulins from plasma/serum (5-20 mg/ml) etc.

Also the composition, i.e., the contents of different types of impurities may vary significantly between different raw materials, e.g., egg yolk has a very different composition as compared to hybridoma cell culture supernatants.

As mentioned above it is generally possible to add different substances to the immunoglobulin containing solution as to enhance the binding of antibodies to the solid phase matrix.

In certain embodiments, the present invention relates to methods for the isolation of immunoglobulins yielding an isolated immunoglobulin of a purity of at least 10% such as at least 30%, preferably at least 50% such as at least 70%, more preferably at least 80% such as 90%, in particular at least 99%.

As mentioned above, it is believed that the binding efficiency maximum pH value for the solid phase matrices is in the range of 2.0 to 10.0, most likely in the range of 3.0 to 9.0. It is therefore most relevant to conduct the isolation process near that maximum (which of course may vary for different combinations of immunoglobulins/solid phase matrices). Thus, the pH of the solution containing the immunoglobulins (or proteins in general) is preferably in the range of 2.0 to 10, such as in the range of 3.0 to 9.0. However, depending on the ligand type and the matrix backbone, the pH range is preferably 3.0 to 7.0 or 6.0 to 9.0.

It is believed that, when the ligand contains an acidic group, the pH of the solution containing the immunoglobulins is preferred to be in the range of 2.0 to 6.0, more preferably in the range of 2.5 to 5.5 such as in the range of 3.0 to 5.5, or in the range of 4.0 to 5.5, corresponding to an expected binding efficiency maximum for that specific type of matrix.

As used herein, an "acidic group" refers to a group having a pKa-value of less than about 6.0.

With respect to contacting step above, it has been found that it is not necessary to add excessive amounts of lyotropic salt in order for the immunoglobulins to bind to the matrix. Thus, the total salt content, including, e.g., NaCl, of the solution containing the immunoglobulins need only be so that it corresponds to a ionic strength of at the most 2.0, preferably in the range of 0.05 to 2.0, such as 0.05 to 1.4, especially in the range of 0.05 to 1.0. As an alternative requirement, the concentration of lyotropic salt as such should be as low as possible, thus, it has been shown that it is possible to operate with a solution containing immunoglobulins where the concentration of lyotropic salts is at the most 0.4 M, preferably at the most 0.3 M, in particular at the most 0.2 M, such as at the most 0.1 M. In a specific embodiment, no lyotropic salt is used.

Examples of lyotropic salts are given in "Purification Tools for Monoclonal Antibodies", Gagnon, P., Validated Biosystems, 1996, where the Hofmeister series of lyotropic ions are presented.

In a specific embodiment, the solution containing one or more immunoglobulins has a pH in the range of 2.0 to 10.0 and a total salt content corresponding to a ionic strength of at the most 2.0.

With respect to the concentration of immunoglobulins in the solution, it is believed that the solid phase matrices can operate for a very large range concentration range, thus, it is believed that the solid phase matrices operate equally efficient for concentration of immunoglobulins in the solution containing the immunoglobulins in the range of 0.001 to 0.2, preferably 0.01 to 0.1, mg/ml, as in hybridoma cell culture supernatants, in the range of 0.2 to 2.0 mg/ml as in milk and whey, in the range of 5.0 to 20 mg/ml as for different animal sera and plasma, and even in the range of 20-80 mg/ml as for colostrum.

It has been found that the present invention is especially suitable for solutions comprising in the range of 0.1 to 30 mg immunoglobulins per gram of solid phase matrix, such as in the range of 0.2 to 2 or in the range of 5.0 to 25 mg per gram of solid phase matrix.

Thus, the solution containing the immunoglobulins may be artificially as well as biologically derived or the like solution of immunoglobulins such as crude fermentation broths; mammalian cell cultures such as hybridoma cell cultures; fermentation broths from cultures of genetically engineered microorganisms such as E. coli; ascites fluids such as mouse and rat ascites fluid; milk, whey, blood, plasma and serum from man, mouse, rat, cow, pig, rabbit, goat, guinea pig, and donkey; and egg yolk such as chicken egg yolk.

Furthermore, high purity of immunoglobulins may be obtained when the solution containing the immunoglobulins comprises a negatively charged detergent. Without being bound to any theory it is believed that the detergent suppresses the adherence of other biomolecules to the matrix. Examples of such detergent are octyl sulfate, bromophenol blue, octane sulfonate, sodium laurylsarcosinate, and hexane sulfonate. In certain embodiments, no negatively charged detergent is used.

Also, in the washing step of the method of the present invention, it is probably for the same reasons, advantageous to use an negatively charged detergent. The detergent may be used alone or in combination with an buffer, e.g., a lyotropic salt buffer. Use of lyotropic salts in the washing step (small volume) represents only a minor waste product problem compared with using lyotropic salts in the binding processes (operation (a)) (in that the binding process includes the use of large volumes is most cases). In certain embodiments, no detergent and lyotropic salts are used in the washing step.

Also, the excellent properties of the solid phase matrices for use in the method according to the invention may be expressed even without the use of organic solvents in the elution step, thus, preferably, the eluent used comprises less than 10% (v/v), more preferably less than 5%, of organic solvents. Most preferably, no organic solvents are used at all.

Alternatively, a larger amount of non-toxic solvents, e.g., propylene glycol, may be used, e.g., up to 40% propylene glycol.

The contacting step as well as the following step, i.e., separation, washing, and elution, may be performed in various way. The physical measures selected are often guided by the scale and whether the process has to be repeated. The solid phase matrices according to the invention may be used in almost any of the set-ups used for development and for industrial purposes. Thus, the solid phase matrix may be contacted with the solution containing the immunoglobulins, e.g., in a stirred batch process, in a packed bed chromatographic column process, or in a fluidized bed process. Further guidelines are given in "Purification Tools for Monoclonal Antibodies", Gagnon, P., Validated Biosystems, 1996.

Other necessary measures for performing the isolation of immunoglobulins according to the invention follow conventional methodologies.

For some applications of immunoglobulins, it is of high important that the immunoglobulins are extremely pure, e.g. having a purity of more than 99%. This is particularly true whenever the immunoglobulin is to be used as a therapeutic, but is also necessary for other applications. In the diagnostic field, the degree of purity needed may depend on a number of factors such as whether the antibody is to be used un-derivatized, in which case there may not be required a high degree of purity, i.e., less than 50%, or whether the antibody has to be labeled with a signal molecule such as an enzyme, e.g., horse-radish peroxidase, in which case the antibody often is required to be at least 80% pure or more. For other applications, the need for purity may differ correspondingly. It seems however to be a general demand that the purity of the immunoglobulin is at least 10% on a dry matter basis to enable a proper use of the product. However, the present invention provides, as it should be clear, guidelines for solving these problems.

It is, as should already be clear from the above, the aim of the present invention to provide solid phase matrices having a high binding efficiency. In addition, solid matrices of the present invention have high stability. More specifically, solid matrices of the present invention are stable in 1 M NaOH, which allows the matrices to be regenerated.

As in the method for the isolation of the immunoglobulins, the total salt content of the solution containing the proteins preferably corresponds to an ionic strength of at the most 2.0, such as in the range of 0.05 to 2.0, in particular in the range of 0.05 to 1.4, especially in the range of 0.05 to 1.0, and/or the concentration of lyotropic salts preferably is at the most 0.4 M, such as at the most 0.3 M, in particular at the most 0.2 M, especially at the most 0.1 M. In certain embodiments, no lyotropic salts are used for the isolation of the immunoglobulins.

The method for the isolation of proteins and other biomolecules may be employed for a number of proteins, examples of which are proteases such as pro-enzymes, trypsins, chymotrypsins, subtilisin, pepsin, plasminogen, papain, renin, thrombin, and elastase; lipases, glucosidases; xylanases; lectins; albumins; proteins from fermentations broths; protein from milk and whey; proteins from blood, plasma, and serum; proteins from fish waste; proteins from slaughterhouse waste such as organ and tissue extracts, e.g., alkaline phosphatase from bovine intestines; and proteins from vegetable extracts such as potato, tomato, coconut, e.g., horse radish peroxidase.

As used herein, the term "alkyl" refers to a saturated straight chain, branched or cyclic hydrocarbon. Preferably, alkyl is a C1-C10 alkyl. Even more preferably, alkyl is a C1-C5 alkyl. The term "C1-C10 alkyl" refers to an alkyl groups with 1-10 carbon atoms which may be straight, branched or cyclic, such as methyl, ethyl, propyl, isopropyl, butyl, isobutyl, tert-butyl, pentyl, hexyl, octyl, dodecyl, cyclopentyl, cyclohexyl, decalinyl, etc. The term "C1-C5 alkyl" refers to an alkyl groups with 1-5 carbon atoms which may be straight, branched or cyclic, such as methyl, ethyl, propyl, isopropyl, butyl, isobutyl, tert-butyl, pentyl, cyclopentyl, etc. Alkyl groups included in compounds of this invention may be optionally substituted with one or more substituents.

The term "optionally substituted alkyl" is intended to mean an alkyl group which may be substituted with one or more, preferably 1-3, groups selected from carboxy; protected carboxy such as a carboxy ester, e.g., (C1-C6)alkoxycarbonyl; aminocarbonyl; mono- and di((C1-C6)alkyl)-aminocarbonyl; amino-(C1-C6)alkyl-aminocarbonyl; mono- and di((C1-C6)alkyl)amino-(C1-C6)alkyl-aminocarbonyl; amino; mono- and di((C1-C6)alkyl)amino; (C1-C6)alkylcarbonylamino; hydroxy; protected hydroxy such as acyloxy, e.g., (C1-C6)alkanoyloxy; sulfono; (C1-C6)alkylsulfonyloxy; nitro; phenyl; phenyl-(C1-C6)alkyl; halogen; nitrilo; and mercapto.

As used herein, the term "alkylene" refers to an alkyl group that has two points of attachment. The term "(C1-C10)alkylene" refers to an alkylene group that has from one to ten carbon atoms. Non-limiting examples of alkylene groups include methylene (—CH₂—), ethylene (—CH₂CH₂—), n-propylene (—CH₂CH₂CH₂—), isopropylene (—CH₂CH(CH₃)—), and the like. The term "(C1-C5)alkylene" refers to an alkylene group that has from one to five carbon atoms. Non-limiting examples of alkylene groups include methylene (—CH₂—), ethylene (—CH₂CH₂—), n-propylene (—CH₂CH₂CH₂—), isopropylene (—CH₂CH(CH₃)—), and the like. Alkylene groups may be optionally substituted with one or more substituents.

As used herein, the term "alkenyl" means an unsaturated straight chain, branched or cyclic hydrocarbon having at least one carbon-carbon double bond. Preferably, alkenyl is a C2-C10 alkenyl. The term "C2-C10 alkenyl" refers to an alkenyl group having 2 to 10 carbon atoms. Representative straight chain and branched (C2-C10)alkenyls include vinyl, allyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, 1-hexenyl, 2-hexenyl, 3-hexenyl, 1-heptenyl, 2-heptenyl, 3-heptenyl, 1-octenyl, 2-octenyl, 3-octenyl, 1-nonenyl, 2-nonenyl, 3-nonenyl, 1-decenyl, 2-decenyl, 3-decenyl and the like. Alkenyl groups may be optionally substituted with one or more substituents.

As used herein, the term "alkenylene" refers to an alkenyl group that has two points of attachment. Alkenylene groups may be optionally substituted with one or more substitutents.

As used herein, the term "alkynyl" means an unsaturated straight chain, branched or cyclic hydrocarbon having at least one carbon-carbon triple bond. Preferably, alkynyl is a C2-C10 alkynyl. The term "C2-C10 alkynyl" refers to an alkynyl group having 2 to 10 carbon atoms. Representative straight chain and branched alkynyls include acetylenyl, propynyl, 1-butynyl, 2-butynyl, 1-pentynyl, 2-pentynyl, 3-methyl-1-butynyl, 4-pentynyl, 1-hexynyl, 2-hexynyl, 5-hexynyl, 1-heptynyl, 2-heptynyl, 6-heptynyl, 1-octynyl, 2-octynyl, 7-octynyl, 1-nonynyl, 2-nonynyl, 8-nonynyl, 1-decynyl, 2-decynyl, 9-decynyl, and the like. Alkynyl groups may be optionally substituted with one or more substituents.

As used herein, the term "alkynylene" refers to an alkynyl group that has two points of attachment. Alkynylene groups may be optionally substituted with one or more substitutents.

As used herein, the term "halogen" refers to —Cl, —F, —Br, or —I.

EXEMPLIFICATION

Example 1

Ligand Synthesis (1) (1H-Benzo[d]imidazol-2-yl)-methanethiol (4)

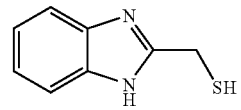 [SMILES: SCc1nc2ccccc2[nH]1]

To 1,2-phenylenediamine (1.88 g, 17 mmol) in 50% v/v hydrochloric acid (20 ml) was added 2-mercaptoacetic acid (1.3 ml, 1.7 g, 19 mmol). The reaction mixture was heated, under nitrogen, at 60° C. then at 90° C. for 48 hours. Additional 2-mercaptoacetic acid (400 µl, 530 mg, 6 mmol) was added in this time. A sample was analyzed by HPLC. The reaction mixture was cooled and neutralized to pH 5 with 40% v/v NaOH. The resulting solid was washed with water (50 ml) and dried under vacuum to yield (1H-Benzo[d]imidazol-2-yl)-methanethiol 1.95 g, 93% yield, Rt=7.6 min, purity >95% together with disulfide (Rt=8.0 mins) 4%. ¹H NMR (d₆-DMSO, 400 MHz) 14.3 ppm (bs, 0.5H), 7.46 ppm (m, 2H), 7.13 (m, 2H), 4.17 ppm (s 0.1H). MS (Electrospray+) 164 m/z (M+), 131 m/z (M−SH).

(2) 5-(2H-Tetrazol-5-yl)-1,3-dihydrobenzoimidazole-2-thione

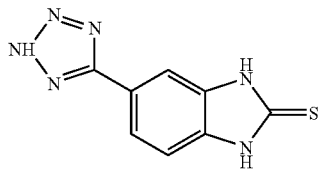 [SMILES: S=c1[nH]c2ccc(-c3nn[nH]n3)cc2[nH]1]

To 4-amino-3-nitrobenzonitrile (4.98 g, 36 mol) in 2-propanol (15 ml) and water (30 ml) was added zinc bromide (13.80 g, 61 mmol) followed by sodium azide (5.81 g, 89 mmol). The reaction mixture was at heated at 80° C. for 10 hours. The reaction was cooled and then analyzed by HPLC. Water (15 ml) was added and the orange colored mixture adjusted to pH 3.0 with 50% (v/v) HCl. The solid was washed with water (50 ml) and dried in an oven at 90° C. to yield an orange yellow colored solid 2-nitro-4-(2H-tetrazol-5-yl)-phenylamine (6.59 g), Rt=8.8 mins, ¹H NMR (d₆-DMSO, 400 MHz) 8.47 ppm (1H, d, 2 Hz), 7.86 ppm (1H, d of d, 9 Hz, 2 Hz), 7.58 ppm (2.3H bs), 6.96 ppm (1H d, 9 Hz). MS (Electrospray+) 206 m/z (M+), 228 m/z (M+Na).

To 2-Nitro-4-(2H-tetrazol-5-yl)-phenylamine (6.80 g) in methanol (450 ml) and 40% (v/v) hydrochloric acid (20 ml) was added 10% Pd on carbon. The reaction vessel was evacuated and charged with hydrogen using a balloon. After 4 hours the reaction was analyzed by HPLC. Water was added (100 ml) and the reaction mixture filtered. The catalyst was washed with 50% v/v methanol in water (100 ml). The solvents were evaporated under reduced pressure (175 mBar then 50 mBar) at 40° C. to yield a brownish colored solid 4-(2H-tetrazol-5-yl)-benzene-1,2-diamine dihydrochloride (6.45 g), Rt=4.9 mins. ¹H NMR (d₆-DMSO, 400 MHz) 7.82 ppm (1H d, 2 Hz), 7.67 ppm (1H, d of d, 8.5 Hz, 2 Hz), 7.03 ppm (1H, d, 8.4 Hz), MS: (Electrospray+) 176.8 m/z (M+), 198.7 m/z (M+Na).

To 4-(2H-tetrazol-5-yl)-benzene-1,2-diamine dihydrochloride (6.40 g, 25 mmol) in acetonitrile (100 ml) was added thiocarbonyl di-imidazole (4.86 g, 28 mmol). A further 100 ml of acetonitrile was added. The reaction was then stirred for 5 hours and the reaction analyzed by HPLC. The solvent was removed under reduced pressure and water added (100 ml). The pH of the reaction mixture was adjusted to pH 2.0 and the solid filtered and washed with water (50 ml). The material was dried to give 5-(2H-tetrazol-5-yl)-1,3-dihydrobenzimidazole-2-thione (3.35 g, 61% yield). The material was suspended in water (300 ml) and the pH adjusted to 11.0 with 40% (v/v) NaOH. Methanol (15 ml) was then added followed by Activated carbon (0.38 g) and the mixture stirred for 1 hour. The mixture was filtered and the solvent removed, under reduced pressure, to half its volume. The pH was adjusted to 2.0 with 50% (v/v) hydrochloric acid to yield an off white solid. The solid was filtered off and washed with water. The purity was >98% by hplc Rt=7.8 mins. The material was dried to yield 5-(2H-tetrazol-5-yl)-1,3-dihydrobenzimidazole-2-thione (2.37 g). ¹H NMR (d₆-DMSO, 400 MHz) 12.88 ppm (1H, s), 12.84 ppm (1H, s), 7.82 ppm (1H, dd, 8.4 Hz, 1.6 Hz), 7.78 ppm (1H, m), 7.30 ppm (1H, d, 8 Hz). MS (high resolution EI). Found 218.036514 m/z C₈H₆N₆S to +4 ppm mass accuracy.

(3) 5-(2H-Tetrazol-5-yl)-1H-benzimidazol-2-yl-amine (1)

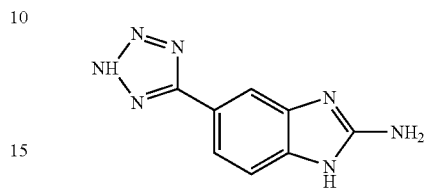

To 4-(2H-tetrazol-5-yl)-benzene-1,2-diamine dihydrochloride (8.56 g, 34 mmol) in water (45 ml) was adjusted to pH 6.0. Cyanogen bromide (3.91 g, 37 mmol) was added and the mixture stirred for 4 hours. The reaction mixture was analyzed by HPLC. The pH of the reaction mixture was adjusted to pH 4.0 with 40% (v/v) sodium hydroxide. The mixture was cooled to 4° C. and the brown solid filtered and washed with water. The material was dried to yield a brown solid 5-(2H-tetrazol-5-yl)-1H-benzimidazol-2y-amine (4.10 g) with a purity of 88%, Rt=7.3 mins. To a suspension of crude 5-(2H-tetrazol-5-yl)-1H-benzimidazol-2ylamine (4.10 g) in water (40 ml), the pH was adjusted to 1.2 with 50% (v/v) hydrochloric acid. Activated carbon was then added (0.2 g) and the mixture stirred for 18 hours. The mixture was filtered and the pH of the filtrate adjusted to pH 3.7 to yield a tan colored solid. The material was dried (3.01 g) and had a purity of >97% by HPLC. ¹H NMR (d₆-DMSO, 400 MHz) 13.04 ppm (0.3H, s), 12.99 ppm (0.3H, s), 8.85 ppm (1H, s), 8.074 ppm (1H, s), 7.96 ppm (dd, 8.4 Hz, 1.2 Hz), 7.55 ppm (d, 8.4 Hz). MS: (Electrospray+) 201.8 m/z (M+), 223.7 m/z (M+Na).

(4) [5-(2H-Tetrazol-5-yl)-1H-benzoimidazol-2-yl]-methanethiol hydrochloride (3)

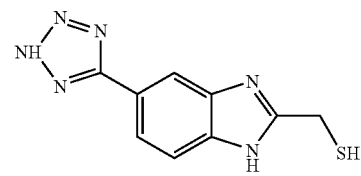

To 4-(2H-tetrazol-5-yl)-benzene-1,2-diamine dihydrochloride (9.40 g, 37.7 mmol) in 50% (v/v) hydrochloric acid (105 ml). 2-mercaptoacetic acid (2.4 ml, 3.18 g, 34.5 mmol) was added and the reaction mixture heated under nitrogen at 110° C. for 48 hours. Additional mercaptoacetic acid (0.5 ml, 0.66 g, 7.20 mmol) was added after 24 hours. The reaction mixture was cooled and a sample analysed by hplc. The greenish coloured solid was filtered off and washed with water. The solid was dried at 50° C. under a vacuum (90 mBar) to yield [5-(2H-tetrazol-5-yl)-1H-benzoimidazol-2-yl]-methanethiol hydrochloride (5.27 g, 65% yield), Rt=7.4 mins, purity by HPLC>97%. ¹H NMR (d₆-DMSO, 400 MHz) 8.49 ppm (1H, m), 8.22 ppm (1H, dd, 8.8 Hz, 1.6 Hz), 7.95

(5) [5-(2H-Tetrazol-5-yl)-1H-benzoimidazol-2-yl]-methylamine (2)

To 4-(2H-tetrazol-5-yl)-benzene-1,2-diamine dihydrochloride (6.40 g, 25.7 mmol) in 50% (v/v) hydrochloric acid (50 ml). Glycine (2.60 g, 34 mmol) was added and the mixture heated to 130° C. for 120 hours. Additional glycine (2.01 g, 26.7 mmol) was added halfway through this period. After this time, the reaction was analyzed by hplc. The pH of the reaction mixture was adjusted to 4.0 with 40% v/v NaOH. The reaction mixture was cooled to 4° C. and the dark colored product filtered off and washed with water (100 ml). The crude product was dried (5.62 g) and had a purity of 93% Rt=7.0 mins. This crude product was suspended in water (50 ml) and the pH adjusted to 1.4 with 50% v/v hydrochloric acid. Activated carbon was then added (0.59 g) and the mixture stirred at 20-25° C. for 18 hours. The carbon was filtered off and washed with water. The pH was adjusted to 4.0 with 40% (v/v) NaOH to yield a light orange solid which was dried under vacuum to yield [5-(2H-tetrazol-5-yl)-1H-benzoimidazol-2-yl]-methylamine (4.22 g). Purity by HPLC >98%. $^1$H NMR ($d_6$-DMSO, 400 MHz) 8.31 ppm (1H, s), 7.96 ppm (1H, d, 6.4 Hz), 7.70 ppm (1H, d, 6.4 Hz), 4.38 (2H, s). MS: (Electrospray+) 216.2 m/z (M+H), 239.2 m/z (M+Na). MS (high resolution EI). Found 215.092339 m/z $C_9H_9N_7$ to −1.8 ppm mass accuracy.

Example 2

Immobilization of Ligands to Solid Phase Backbone

General Procedure

To ligand (4.1 mmol) in NMP (2 ml) was added water (7 ml) followed by bromine activated allylated cross linked agarose (10 ml, 150 µmol/ml of allyl groups). 10M sodium hydroxide (1 ml) was then added and the mixture rolled for 18 hours at 20-25° C. [For ligands containing thiol functional groups a small amount of $NaBH_4$ was added]. The gel was washed with 10 cv of NMP, water, 0.5M HCl, water, 0.5M NaOH and then 20 cv water. The filtrate ligand was analyzed by HPLC. The gel was suspended in 50% ethanol containing 0.5M HCl then washed with 10 cv ethanol, water, 0.5M NaOH and 20 cv water. The gels were analyzed by acidometric titration and elemental analysis.

5-(2H-Tetrazol-5-yl)-1H-benzimidazol-2-yl-amine (1)

To 5-(2H-Tetrazol-5-yl)-1H-benzimidazol-2-yl-amine (838 mg, 4.1 mmol) in NMP (2 ml) and water (7 ml) was added 10 ml bromine activated allylated [150 µmol/ml of allyl groups] cross linked 6% agarose followed by 10M sodium hydroxide (1 ml). The mixture was rolled for 18 hours at 20-25° C. The gel was washed with 10 cv of NMP, water, 0.5M HCl, water, 0.5M NaOH and then 20 cv water. The filtrate ligand was analysed by hplc. The gel was suspended in 50% ethanol containing 0.5M HCl then washed with 10 cv ethanol, water, 0.5M NaOH and 20 cv water. Titration gave a value of 77 µmol/ml, elemental analysis gave 61 µmol/ml based on nitrogen.

5-(2H-Tetrazol-5-yl)-1,3-dihydrobenzoimidazole-2-thione

Similar to the procedure described above using (676 mg, 4.1 mmol) of 5-(2H-Tetrazol-5-yl)-1,3-dihydrobenzoimidazole-2-thione and $NaBH_4$ (3 mg). Titration gave a value of 133 µmol/ml, elemental analysis gave 177 µmol/ml based on nitrogen.

[5-(2H-Tetrazol-5-yl)-1H-benzoimidazol-2-yl]-methanethiol hydrochloride (3)

Similar to the procedure described above using (1.142 g, 4.2 mmol) of [5-(2H-Tetrazol-5-yl)-1H-benzoimidazol-2-yl]-methanethiol hydrochloride and $NaBH_4$ (3 mg). Titration gave a value of 78 µmol/ml, elemental analysis gave 61 µmol/ml based on nitrogen.

[5-(2H-Tetrazol-5-yl)-1H-benzoimidazol-2-yl]-methylamine (2)

Similar to the procedure described above using (545 mg, 4.6 mmol) of [5-(2H-Tetrazol-5-yl)-1H-benzoimidazol-2-yl]-methylamine. Titration gave a value of 76 µmol/ml, elemental analysis gave 49 µmol/ml based on nitrogen.

Solid matrices with 2-aminobenzimidazole or 1H-benzo[d]imidazole-2,6-diamine (5) as ligand were prepared according to the procedures described above.

Example 3

Immunoglobulin Binding Capacity and Purity Measurements

Static hIgG Capacity Measurement.

Two disposable columns were packed with 2 mL of ligand-agarose sample (46 mm above the column frit) for each matrix sample to be tested including one reference column. The agarose was allowed to settle under gravity in PBS buffer at pH 7.4. The columns were labeled appropriately.

350 mg of human IgG was dissolved in 7 mL PBS buffer at pH 7.4 for each column to be tested. The human IgG solution was filtered through 0.22 µm filters.

A 1:50 dilution of the filtered IgG solution was prepared by serial dilution and the concentration of IgG was calculated as follows:

concentration of human IgG (mg/mL)=$OD_{280\ nm} \times 50/1.38$

The IgG solution has a concentration of 35-45 mg/mL.

Each column was washed with 4×5 mL of PBS buffer. 5 mL of the IgG solution was loaded to each column and collect the flowthrough (FT) in a glass universal. Each column was washed with 4×5 mL of PBS buffer to remove any unbound IgG and the wash was collected into the universal containing the flowthrough.

The bound IgG was eluted with 10 mL of 0.1 M glycine/HCl buffer pH 2 and the elution was collected in a glass universal.

The two universals were mixed for about 5 minutes.

The $OD_{280\ nm}$ of IgG in each universal was measured using the spectrophotometer and a 1.5 mL quartz cuvette. PBS was used as blank when measuring the flowthrough and wash and 0.1 M glycine/HCl buffer was used as blank when measuring the elution.

The volume of ligand-agarose in the column was determined by measuring the bed height (mm). Percentage of recovery was calculated by the sum of IgG in the flowthrough, wash and elution divided by the total amount of IgG loaded. IgG capacity (mg/mL) was calculated by the amount of IgG in elution divided by the column volume. Ligand utilization value (mg/ml) was calculated by dividing the amount of IgG eluted with the amount of ligand (mg) in the matrix.

Polyclonal Dynamic Capacity Measurement.

Using a standard Dynamic capacity method (20% BT, 10% BT+10% non-binding) and standard buffers, 2 ml of each sample was packed into an Omnifit column and hIgG was applied to 20% breakthrough. The protein was then eluted and the column cleaned, the $OD_{280}$ of the elution was measured and the volume of hIgG applied was noted. Measurement conditions are listed below:

| | |
|---|---|
| Flow rate | 2.5 min res time (0.8 ml/min) |
| Equilibration buffer | PBS pH 7.4 |
| Load | 1 mg/ml IgG PBS pH 7.4 |
| Wash | PBS pH 7.4 |
| Elution | 0.1M Glycine pH 2 |
| Clean | 0.5M NaOH |

The amount of IgG required to achieve 20% BT was determined by the following procedure.

A solution of IgG was passed through a test column containing solid phase matrix of interest in bypass mode until a plateau level was reached. The amount of IgG is measured in terms mAU. An amount of IgG equal to 20% of the amount of IgG in the flowthrough was loaded onto another column packed with the solid phase matrix followed by washing and eluting IgG from the column.

Feedstock Capacity Assay

Using a standard feedstock method and standard buffers, 2 ml of each sample was packed into an Omnifit column (0.66 cm) and Anti-nip feedstock was applied until 20% breakthrough was reached (as determined by a separate Protein A column). The protein was then eluted and the column cleaned. Assay conditions are listed below:

| | |
|---|---|
| Flow rate | 2.5 min res time (0.8 ml/min) |
| Equilibration buffer | PBS pH 7.4 |
| Load | Anti-nip (wave 74&75) pH 7.4 |
| Wash | PBS pH 7.4 |
| Elution | 0.1M Sodium Citrate pH3 |
| Clean | 0.5M NaOH |

The amount of anti-nip feedstock required to achieve 20% BT was determined by the following procedure.

The Anti-nip feedstock was loaded onto a test column containing solid phase matrix of interest until the flowthrough reached a plateau. The flowthrough was collected in aliquots and analyzed for IgG content (using a Protein A affinity column). The 100% BT was determined when mAu of IgG in the start feedstock (analyzed on a Protein A affinity column) is equal to mAu of IgG in the flow through from the test column. An amount of Anti-nip feedstock corresponding to 20% BT was loaded onto another column packed with solid phase matrix of interest followed by washing and eluting IgG from the column.

Impurity Binding Study with CHO Medium 5

CHO Medium 5 was used to study color binding and impurity binding of the matrices of the present invention. The breakthrough (BT) and wash, the elution, the clean (with 1% hexadecyltrimethylammonium bromide (hexa), pH 1.5) and a final 0.5M NaOH wash were collected and values of the $OD_{280\ nm}$ were recorded.

Measurement 1. 1 ml of each matrix sample was measured in a small gravity fed column and equilibrated using 15 ml PBS pH 7.4
2. 10 ml of CHO Medium 5 was applied and allowed to drip through, the BT was collected in a universal, 1 ml of PBS was then applied and this flow through (FT) was collected in the same vessel.
3. 10 ml of the elution buffer 0.1 M glycine pH 2 was applied and the FT was collected
4. 10 ml of the hexa, pH 1.5 was applied and collected to clean the matrix.
5. 10 ml of 0.5M NaOH was then applied and collected to ensure all the bound contaminants had been washed off, this will enable a mass balance to be calculated.
6. The $OD_{280\ nm}$ was then read for all the samples and to enable a direct comparison. The $OD_{280\ nm}$ values were converted into percentages of the total $OD_{280\ nm}$ obtained.

Interpreting the Data

1. The $OD_{280\ nm}$ was read for each sample at each stage i.e, BT+W, elution, clean and NaOH wash
2. This value was then multiplied by any dilution factors.
3. The OD value after adjusted with dilution factor was then multiplied by the number of ml in the fraction i.e 20 ml for BT+W, 10 ml for the other steps.
4. A total OD was then calculated as the sum of OD value for each fraction multiplied by the number of ml in each fraction.
5. The total OD was then used to calculate the % of contaminants in each stage.

Example 4

Binding Performance of Matrices of the Present Invention

Static Capacities

The static capacity for matrix with ligands 1, 2, 3, 4 or 5 (samples 1, 2, 3, 4 or 5) was measured according to the procedure described above. Static capacity for solid phase matrix with 2-aminobenzimidazole as ligand L was also measured as control.

Tables 1-5 summarize the static capacity data.

TABLE 1

Static IgG binding capacity for sample 1.

| Sample | Static Capacity (mg/ml) | % elution recovery | ligand (µmol/ml) | IgG binding (mg IgG/µmol ligand) |
|---|---|---|---|---|
| control | 65 | 95 | 115 | 0.6 |
| 1 | 68 | 90 | 77 | 0.9 |

TABLE 2

Static IgG binding capacity for sample 2.

| Sample | Static Capacity (mg/ml) | % elution recovery | ligand (μmol/ml) | IgG binding (mg IgG/μmol ligand) |
|---|---|---|---|---|
| control | 63 | 103 | 97 | 0.7 |
| 2 | 58 | 102 | 76 | 0.76 |

TABLE 3

Static IgG binding capacity for sample 3.

| Sample | Static Capacity (mg/ml) | % elution recovery | ligand (μmol/ml) | IgG binding (mg IgG/μmol ligand) |
|---|---|---|---|---|
| control | 66 | 101 | 107 | 0.62 |
| 3 | 52 | 103 | 78 | 0.67 |

TABLE 4

Static IgG binding capacity for sample 4.

| Sample | Static Capacity (mg/ml) | % elution recovery | ligand (μmol/ml) | IgG binding (mg IgG/μmol ligand) |
|---|---|---|---|---|
| control | 69 | 95 | 114 | 0.61 |
| 4 | 55 | 103 | 118 | 0.47 |

TABLE 5

Static IgG binding capacity for sample 5.

| Sample | Static Capacity (mg/ml) | % elution recovery | ligand (μmol/ml) | IgG binding (mg IgG/μmol ligand) |
|---|---|---|---|---|
| control | 65 | 95 | 115 | 0.6 |
| 5 | 44 | 93 | 40 | 1.1 |

As shown in Tables 1-5, samples 1-5 have comparable or superior static binding capacity comparing to control sample. Specifically, samples 1 and 5 have a much higher ligand utilization value comparing to the control sample.

Feedstock Capacity

Feedstock capacities for samples 1-5 were measured using anti-nip feedstock and the data are summarized in Table 6. Feedstock capacity for solid phase matrix with 2-aminobenzimidazole as ligand was also measured as control. Purity of the IgG eluted were determined by using PrA column. Purity percentage is calculated by the amount of IgG bound to a PrA column divided by the total amount of IgG eluted, determined by measuring $OD_{280\ nm}$.

TABLE 6

Feedstock IgG binding capacity for samples 1-5.

| sample | Frontal analysis DBC 20% BT, 2.5 min RT (mg/ml) | Elution (mg IgG/ml) | % IgG Purity |
|---|---|---|---|
| control | 31 | 34 | 64 |
| 1 | 31 | 34 | 70 |
| 2 | 26 | 12 | 74 |
| 3 | 38 | 12 | 80 |

TABLE 6-continued

Feedstock IgG binding capacity for samples 1-5.

| sample | Frontal analysis DBC 20% BT, 2.5 min RT (mg/ml) | Elution (mg IgG/ml) | % IgG Purity |
|---|---|---|---|
| 4* | 24, 24 | 29, 38 | 46, 68 |
| 5 | 27 | 45 | 60 |

*based on two determinations.

As shown in Table 6, samples 1 and 5 have similar anti-nip capacity comparing to the control. However, IgG purity eluted from Sample 1 is higher than that eluted from the control sample. Samples 2 and 3 has similar frontal analysis values and lower elution values comparing to those for the control sample, indicating samples 2 and 3 bind to IgG stronger than the control sample. The purity of IgG eluted from samples 2 and 3, however, are significantly higher than the control sample. Sample 4 has a slightly lower anti-nip binding capacity comparing to the control sample.

Impurity binding of samples 1-5 were also compared with that of the control sample by visualizing the color of elution solution (solution eluted with 0.1 M sodium citrate at pH 3) and the color of strip solution (solution collected with 0.5 M NaOH wash). The elution solution and strip solution for control sample were cloudy and yellow. The elution solution and strip solution for sample 1 were clear and slightly yellow. The elution solution for sample 2 was clear and slightly yellow. The elution solution for sample 3 was clear and colorless. The elution solution for sample 4 was colorless and slightly cloudy. The elution solution for sample 5 was clear and colorless. Therefore, samples 1-5 had less color binding than that of the control.

Polyclonal Dynamic Binding Capacity

Polyclonal dynamic binding capacities for samples 1-4 were measured and compared to the control sample (solid phase matrix with 2-aminobenzimidazole as ligand L). The binding capacity data at room temperature with 20% BT and 2.5 min residence time, are listed in Table 7.

TABLE 7

Polyclonal IgG dynamic binding capacity data for samples 1-5 and control sample.

| sample | Frontal analysis (mg/ml) | Elution (mg/ml) |
|---|---|---|
| control | 39 | 34 |
| 1 | 34 | 27 |
| 2 | 19 | 17 |
| 3 | 19 | 6 |
| 4 | 29 | 26 |
| 5 | 30 | 21 |

Samples 1 and 4 have similar or slightly lower polyclonal dynamic binding capacities comparing to the control sample.

Impurity Binding with CHO 5 Medium

Impurity binding of samples 1, 2 and 4 were measured using CHO 5 medium. Impurity binding of the control sample and XL allylated agarose beads (agarose beads which have no ligand immobilized but were put through immobilization procedure) were also measured. The binding data are summarized in Tables 8-10.

TABLE 8

Impurity binding data for sample 1, control sample and XL allylated agarose using CHO 5 medium.

|  | Total | % BT | % Elution | % Clean | % NaOH strip | total contaminants bound (%) |
|---|---|---|---|---|---|---|
| XL allylated | 97.66 | 97.3 | 1.45 | 0.9 | 0.3 | 2 |
| control | 90.47 | 75.8 | 20.34 | 2.5 | 1.3 | 23 |
| 1 | 90.99 | 85.1 | 10.65 | 2.5 | 1.8 | 13 |

TABLE 9

Impurity binding data for sample 2, control sample and using CHO 5 medium.

|  | Total | % BT | % Elution | % Clean | % NaOH strip | total contaminants bound (%) |
|---|---|---|---|---|---|---|
| control | 86.27 | 74.9 | 20.29 | 4.0 | 0.82 | 25.12 |
| 2 | 95.58 | 98.1 | 1.22 | 0.6 | 0.08 | 1.86 |

TABLE 10

Impurity binding data for sample 4, control sample and using CHO 5 medium.

|  | Total | % BT | % E | % Hexa | NaOH | total contaminants bound (%) |
|---|---|---|---|---|---|---|
| Control | 97.13 | 75.4 | 18.78 | 5.9 | 0.00 | 24.64 |
| 4 | 101.39 | 96.3 | 2.06 | 1.7 | 0.00 | 3.74 |

As shown in Tables 8-10, samples 1, 2, and 4 bind significantly less impurities comparing to the control sample.

All references referred to herein are incorporated by reference in their entirety.

While this invention has been particularly shown and described with references to example embodiments thereof, it will be understood by those skilled in the art that various changes in form and details may be made therein without departing from the scope of the invention encompassed by the appended claims.

What is claimed is:

1. A method for isolation of immunoglobulins from a solution containing one or more immunoglobulins, comprising:
   a) contacting the solution containing one or more immunoglobulins with a solid phase matrix of the general formula

M-SP-L, wherein M designates the matrix backbone, SP designates a spacer, and L designates a ligand represented by the structural formula (II):

(II)

or a tautomer thereof, wherein
   $R_1$ is —Z—N($R_3$)$_2$;
   $R_2$ is —H, -halogen, —O$R_4$, —NH$_2$, -alkyl, —NO$_2$, —SO$_3$H, —N($R_3$)C(O)N($R_3$)$_2$, , or ;

$R_3$, for each occurrence, is independently —H or a substituted or unsubstituted alkyl;
   $R_4$, for each occurrence, is independently —H or a substituted or unsubstituted alkyl;
   $R_5$, for each occurrence, is independently —H or a substituted or unsubstituted alkyl;
   Z is a single bond, an optionally substituted alkylene, a substituted or unsubstituted alkenylene or a substituted or unsubstituted alkynylene; and
   n is an integer from 0 to 4;
   b) separating the solid phase matrix having immunoglobulins bound thereto from the solution;
   c) optionally washing the solid phase matrix; and
   d) contacting the solid phase matrix with an eluent in order to liberate the one or more immunoglobulins from the solid phase matrix, thereby isolating the immunoglobulin.

2. The method of claim 1, wherein L designates a ligand represented by the following structural formula:

(III)

or or a tautomer thereof.

3. The method of claim 2, wherein $R_5$ is —H.

4. The method of claim 1, wherein Z is a single bond and n is 1.

5. The method of claim 4, wherein $R_3$ is —H.

6. The method of claim 1, wherein L designates a ligand represented by one of the following structural formulas:

1

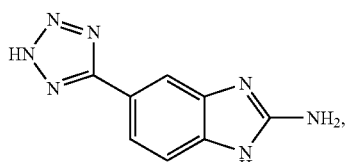

2

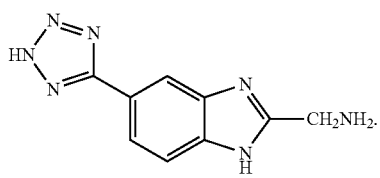

7. The method of claim 1, wherein the pH of the solution containing one or more immunoglobulins is in the range of 6.0 to 10.0.

8. The method of claim 1, wherein the matrix backbone is agarose.

9. The method of claim 1, wherein the spacer SP is represented by the following formula:

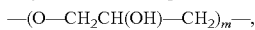

wherein m is an integer from 1 to 10.

10. The method of claim 1, wherein:
the matrix backbone is agarose;
the spacer SP is represented by the following formula:

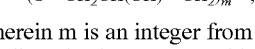

wherein m is an integer from 1 to 3; and
the ligand L is represented by one of the following structural formulas:

1

2

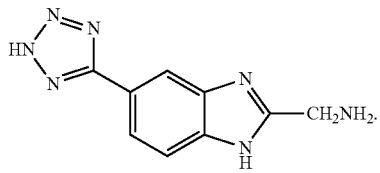

11. The method of claim 1, wherein the solution containing one or more immunoglobulins has a pH in the range of 2.0 to 10.0.

12. The method of claim 11, wherein the solution containing one or more immunoglobulins has a total salt content corresponding to an ionic strength of at the most 2.0, and lyotropic salts in a concentration of at the most 0.4 M.

13. The method of claim 12, wherein the solution containing one or more immunoglobulins has no lyotropic salt.

14. A method for isolation of immunoglobulins from a solution containing one or more immunoglobulins, comprising:
a) contacting the solution containing one or more immunoglobulins with a solid phase matrix of the general formula

M-SP-L, wherein M designates the matrix backbone, SP designates a spacer, and L designates a ligand represented by the structural formula (II):

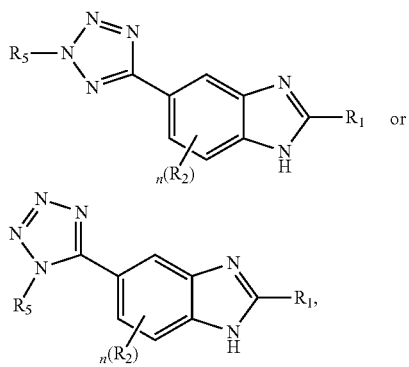

(II)

or a tautomer thereof, wherein $R_1$ is —Z—$SR_3$;

$R_2$ is —H, -halogen, —$OR_4$, —$NH_2$, -alkyl, —$NO_2$, —$SO_3H$, —$N(R_3)C(O)N(R_3)_2$,

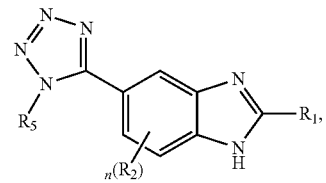

$R_3$, for each occurrence, is independently —H or a substituted or unsubstituted alkyl;

$R_4$, for each occurrence, is independently —H or a substituted or unsubstituted alkyl;

$R_5$, for each occurrence, is independently —H or a substituted or unsubstituted alkyl;

Z is a single bond, an optionally substituted alkylene, a substituted or unsubstituted alkenylene or a substituted or unsubstituted alkynylene; and n is an integer from 0 to 4;

b) separating the solid phase matrix having immunoglobulins bound thereto from the solution;

c) optionally washing the solid phase matrix; and d) contacting the solid phase matrix with an eluent in order to liberate the one or more immunoglobulins from the solid phase matrix, thereby isolating the immunoglobulin.

15. The method of claim 14, wherein L designates a ligand represented by the following structural formula:

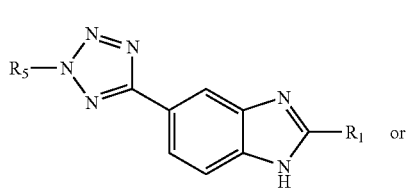

(III)

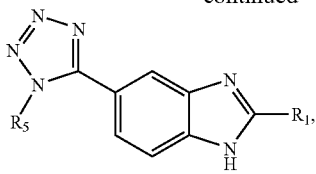

or a tautomer thereof.

16. The method of claim 15, wherein $R_5$ is —H.
17. The method of claim 14, wherein L designates a ligand represented by the following structural formula:

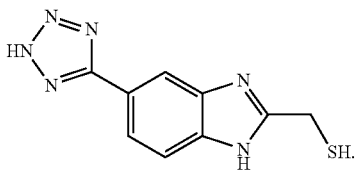

18. The method of claim 14, wherein the pH of the solution containing one or more immunoglobulins is in the range of 2.0 to 10.0.
19. The method of claim 14, wherein the matrix backbone is agarose.
20. The method of claim 14, wherein the spacer SP is represented by the following formula:

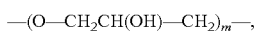

—(O—CH$_2$CH(OH)—CH$_2$)$_m$—, wherein m is an integer from 1 to 10.
21. The method of claim 14, wherein:
the matrix backbone is agarose;
the spacer SP is represented by the following formula:

—(O—CH$_2$CH(OH)—CH$_2$)$_m$-, wherein m is an integer from 1 to 3; and the ligand L is represented by the following structural formula:

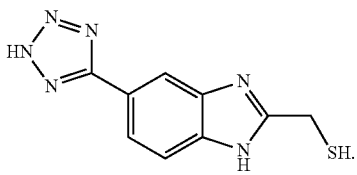

22. The method of claim 18, wherein the solution containing one or more immunoglobulins has a total salt content corresponding to an ionic strength of at the most 2.0, and lyotropic salts in a concentration of at the most 0.4 M.
23. A method for isolation of immunoglobulins from a solution containing one or more immunoglobulins, comprising:
a) contacting the solution containing one or more immunoglobulins with a solid phase matrix of the general formula

M-SP-L, wherein M designates the matrix backbone, SP designates a spacer, and L designates a ligand represented by the structural formula (II):

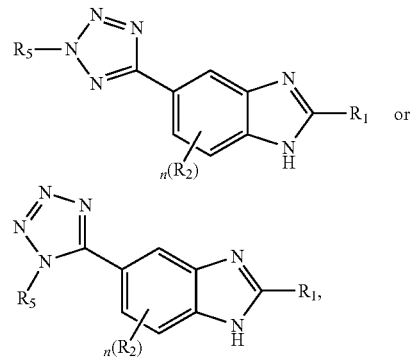

or a tautomer thereof, wherein
$R_1$ is —Z—OR$_3$;
$R_2$ is —H, -halogen, —OR$_4$, —NH$_2$, -alkyl, —NO$_2$, —SO$_3$H, —N(R$_3$)C(O)N(R$_3$)$_2$,

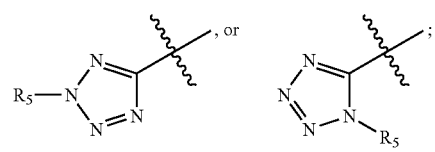

$R_3$, for each occurrence, is independently —H or a substituted or unsubstituted alkyl;
$R_4$, for each occurrence, is independently —H or a substituted or unsubstituted alkyl;
$R_5$, for each occurrence, is independently —H or a substituted or unsubstituted alkyl;
Z is a single bond, an optionally substituted alkylene, a substituted or unsubstituted alkenylene or a substituted or unsubstituted alkynylene; and
n is an integer from 0 to 4;
b) separating the solid phase matrix having immunoglobulins bound thereto from the solution;
c) optionally washing the solid phase matrix; and
d) contacting the solid phase matrix with an eluent in order to liberate the one or more immunoglobulins from the solid phase matrix, thereby isolating the immunoglobulin.
24. The method of claim 23, wherein L designates a ligand represented by the following structural formula:

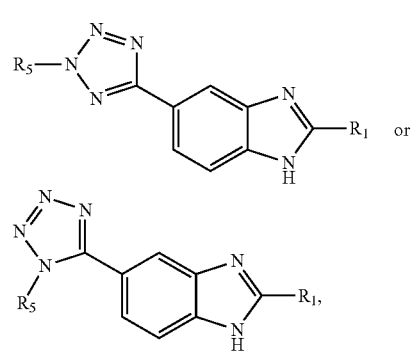

or a tautomer thereof.

25. The method of claim 24, wherein $R_5$ is —H.

26. The method of claim 23, wherein the pH of the solution containing one or more immunoglobulins is in the range of 2.0 to 10.0.

27. The method of claim 23, wherein the matrix backbone is agarose.

28. The method of claim 23, wherein the spacer SP is represented by the following formula:

$$-(O-CH_2CH(OH)-CH_2)_m-,$$

wherein m is an integer from 1 to 10.

29. The method of claim 26, wherein the solution containing one or more immunoglobulins has a total salt content corresponding to an ionic strength of at the most 2.0, and lyotropic salts in a concentration of at the most 0.4 M.

30. The method of claim 14, wherein Z is a single bond; n is 1; and $R_3$ is —H.

31. The method of claim 23, wherein Z is a single bond; n is 1; and $R_3$ is —H.

* * * * *